US010925974B2

(12) United States Patent
Yuan et al.

(10) Patent No.: US 10,925,974 B2
(45) Date of Patent: Feb. 23, 2021

(54) ADIPOSE TISSUE-TARGETING POLYPEPTIDE-VERBASCOSIDE-NANOGOLD PARTICLE DERIVATIVE, PREPARATION METHOD AND APPLICATION THEREOF

(71) Applicants: Affiliated Stomatological Hospital of Nanjing Medical University, Nanjing (CN); Nanjing Medical University, Nanjing (CN)

(72) Inventors: Yi Yuan, Nanjing (CN); Yaqin Zhang, Nanjing (CN); Hongwei Li, Nanjing (CN); Jindao Wu, Nanjing (CN); Heming Wu, Nanjing (CN); Liyong Pu, Nanjing (CN)

(73) Assignees: Affiliated Stomatological Hospital of Nanjing Medical University, Nanjing (CN); Nanjing Medical University, Nanjing (CN)

( * ) Notice: Subject to any disclaimer, the term of this patent is extended or adjusted under 35 U.S.C. 154(b) by 46 days.

(21) Appl. No.: 16/261,137

(22) Filed: Jan. 29, 2019

(65) Prior Publication Data

US 2019/0167807 A1 Jun. 6, 2019

(30) Foreign Application Priority Data

Jun. 6, 2018 (CN) .......................... 2018 1 0573603

(51) Int. Cl.
| | |
|---|---|
| *A61K 47/64* | (2017.01) |
| *A61K 47/60* | (2017.01) |
| *A61K 47/69* | (2017.01) |
| *A61P 3/04* | (2006.01) |
| *A61K 9/51* | (2006.01) |
| *A61K 36/53* | (2006.01) |
| *B82Y 5/00* | (2011.01) |
| *A61K 9/00* | (2006.01) |

(52) U.S. Cl.
CPC ............ *A61K 47/6929* (2017.08); *A61K 9/51* (2013.01); *A61K 36/53* (2013.01); *A61K 47/60* (2017.08); *A61K 47/64* (2017.08); *A61K 47/6923* (2017.08); *A61P 3/04* (2018.01); *A61K 9/0019* (2013.01); *B82Y 5/00* (2013.01)

(58) Field of Classification Search
CPC combination set(s) only.
See application file for complete search history.

(56) References Cited

FOREIGN PATENT DOCUMENTS

CN 102120755 A 7/2011

OTHER PUBLICATIONS

Xuli Wu et al Acteoside: a lipase inhibitor from the Chinese tea Ligustrum purpurascens kudingcha, Food Chem (2014) Jan. 1;142: 306-10 (Year: 2014).*
Mikhail G Kolonin, Pradip K Saha, Lawrence Chan, Renata Pasqualini, Wadih Arap; Reversal of obesity by targeted ablation of adipose tissue; Nature Medicine; Jun. 2004; pp. 625-632; vol. 10 | No. 6; Nature Publishing Group http://www.nature.com/naturemedicine.

* cited by examiner

*Primary Examiner* — Thomas S Heard
(74) *Attorney, Agent, or Firm* — Dragon Sun Law Firm, PC; Jinggao Li, Esq.

(57) ABSTRACT

Embodiments of the present disclosure provides a method of preparing an adipose tissue-targeting polypeptide-verbascoside-nanogold particle derivative, including: activating a carboxyl group of a cysteine residue at the C-terminus of an adipose tissue-targeting polypeptide to form an acyl chloride; reacting a verbascoside with a sodium hydroxide to obtain a sodium phenolate; esterifying the acyl chloride with the sodium phenolate to form an adipose tissue-targeting polypeptide-verbascoside derivative; and reacting the adipose tissue-targeting polypeptide-verbascoside derivative with PEG-modified nanogold particles. The present disclosure further discloses an adipose tissue-targeting polypeptide-verbascoside-nanogold particle derivative and the application of the adipose tissue-targeting polypeptide-verbascoside-nanogold particle derivative in preparing a drug for the treatment of obesity. The adipose tissue-targeting polypeptide-verbascoside-nanogold particle derivative has good biocompatibility, and capable of carrying drugs into the adipocytes, thereby greatly enhancing the availability of the drug and significantly improving the targeted anti-obesity activity of the drug.

7 Claims, 2 Drawing Sheets
Specification includes a Sequence Listing.

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Amino Acid Sequence of adipose tissue-targeting polypeptide
<220> FEATURE:
<221> NAME/KEY: PEPTIDE
<222> LOCATION: (1)..(9)

```
<400> SEQUENCE: 1

Cys Lys Gly Gly Arg Ala Lys Asp Cys
1               5
```

ADIPOSE TISSUE-TARGETING POLYPEPTIDE-VERBASCOSIDE-NANOGOLD PARTICLE DERIVATIVE, PREPARATION METHOD AND APPLICATION THEREOF

CROSS REFERENCE TO RELATED APPLICATION

This application is based upon and claims priority to Chinese Patent Application No. 201810573603.9, filed on Jun. 6, 2018. The entire disclosure of the above-identified application is incorporated herein by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

REFERENCE TO SEQUENCE LISTING

The present application is being filed along with a Sequence Listing in electronic format. The Sequence Listing is provided as a file entitled SEQUENCE LIST ST25.TXT, created Jun. 23, 2019, which is 742 bytes in size. The information in the electronic format of the Sequence Listing is incorporated herein by reference in its entirety.

TECHNICAL FIELD

The present disclosure relates to a targeting polypeptide, and especially relates to an adipose tissue-targeting polypeptide-verbascoside-nanogold particle derivative, preparation method and application thereof.

BACKGROUND

In recent years, due to dietary changes, sedentary working mode, reduced amount of exercise, and a westernized lifestyle, the number of obese patients in China has increased rapidly. Obesity is a chronic metabolic disease caused by excessive accumulation of white fat (including visceral fat and subcutaneous fat) due to greater energy intake than energy consumption. It can be divided into two categories including central obesity (abdominal obesity, mainly noted as visceral fat accumulation) and simple obesity (mainly noted as subcutaneous fat accumulation). A great number of studies have found that obesity due to excess white fat is a major cause of metabolic diseases such as insulin resistance, type 2 diabetes, hyperlipidemia, hypertension, etc. In addition, obesity is not only associated with metabolic diseases, but also closely related to the occurrence and progress of certain types of tumors. Therefore, intervention treatments of obesity, especially for white fat, are important measures to prevent and treat the obesity-related diseases.

At present, the main treatments for obesity include dietary behavior therapies, surgeries and drug therapies. For most of obese patients, reducing energy intake and increasing amount of exercise can help them lose weight. However, when they stop these measures of losing weight, the weight will rebound, and even surpass the weight prior to taking these measures. Further, surgeries (such as gastrectomy, gastric bypass surgery, or gastric banding surgery) are too risky. Accordingly, medication becomes a top choice for many obese patients. FDA of U.S. has approved two long-term weight-loss drugs, i.e., Sibutramine and Orlistat. However, with long-term medication, the former one may cause hypertension, insomnia, etc., while the latter one may cause serious gastrointestinal side effects, such as diarrhea, fecal incontinence, etc., which limits drug usage. Therefore, how to make drugs only act on the adipose tissue, without affecting other organs and tissues related to metabolic syndromes, so as to treat the metabolic syndromes more efficiently without interference with the human immune system, has become a key topic of the obesity treatment.

In 2004, the well-known scientific journal "*Nature Medicine*" reported that a polypeptide having an amino acid sequence of CKGGRAKDC, could bind with prohibitin (endothelial cell receptors) in white adipose tissue vessels, and thus can target white adipose tissue vessels. To test whether the polypeptide can carry materials having pharmacological effects and bioactivity targeting the white adipose tissue vessels, angiogenesis is inhibited through destruction of structures of the adipose tissue vessels, thereby inhibiting obesity due to accumulation of adipose. The targeting polypeptide is connected to $(KLAKLAK)_2$ through glycinylglycine bridge to form CKGGRAKDC-GG-$_D$(KLAKLAK)$_2$ of targeted adipose tissue vessels having 25 residues. However, CKGGRAKDC-GG-$_D$(KLAKLAK)$_2$ formed by connecting the targeting polypeptide and $(KLAKLAK)_2$ limits drug loading of the targeting polypeptide. Specifically, in terms of the structural formula of the targeting polypeptide, one molecule of the targeting polypeptide can only carry one molecule of $(KLAKLAK)_2$ to enter into adipose tissues, so that higher injection dose is required for the same drug effect, thereby increasing therapy costs. Thus, the effect of the prior art technologies for treatment of obesity is limited, thereby limiting the general usage of targeting drugs for treatment of obesity. Further, variety of drugs carried by the targeting polypeptide and biological safety of polypeptide-drug compound are key pending issues during treatment of obesity. Thus, in terms of drawbacks in the prior art, there is a desire to develop a new targeting carrier carrying drugs for safe and effective treatment of obesity, and a heretofore unaddressed need exists in the art to address the aforementioned deficiencies and inadequacies.

SUMMARY OF THE DISCLOSURE

One objective of the present disclosure is to develop a targeting carrier which can carry various drugs and have a high drug loading. Embodiments of the present disclosure provide a preparation method of the adipose tissue-targeting polypeptide-verbascoside-nanogold particle derivative. Embodiments of the present disclosure further provides an adipose tissue-targeting polypeptide-verbascoside-nanogold particle derivative. Embodiments of the present disclosure further provide the application of the adipose tissue-targeting polypeptide-verbascoside-nanogold particle derivative in preparing drugs for obesity.

Embodiments of the present disclosure provide a preparation method of an adipose tissue-targeting polypeptide-verbascoside-nanogold particle derivative, including the following steps:

(1) activating a carboxyl group of a cysteine residue at the C-terminus of an adipose tissue-targeting polypeptide to form an acyl chloride; wherein the adipose tissue-targeting polypeptide has an amino acid sequence of CKGGRAKDC;

(2) reacting a verbascoside with a sodium hydroxide to obtain a sodium phenolate;

(3) esterifying the acyl chloride obtained in step (1) with the sodium phenolate obtained in step (2) to form an adipose tissue-targeting polypeptide-verbascoside derivative;

(4) modifying a nanogold particle with PEG (polyethylene glycol), mixing and reacting the adipose tissue-targeting polypeptide-verbascoside derivative obtained in step (3) with PEG-modified nanogold particles; wherein the sulfydryl of the cysteine residue at the C-terminus of the adipose tissue-targeting polypeptide is connected to the nanogold particles with an Au—S bond.

In a further embodiment, at the step (1), the amino acid residues represented by alphabetic symbols in the amino acid sequence of the adipose tissue-targeting polypeptide are defined as follows: C is cysteine, K is lysine, G is glycine, R is arginine, A is alanine, and D is aspartic acid. A first amino protecting group is connected to a side chain of the second amino acid residue of the adipose tissue-targeting polypeptide, and a second amino protecting group is connected to the seventh amino acid residue of the adipose tissue-targeting polypeptide. A guanidine protecting group is connected to the fifth amino acid residue (arginine). A carboxyl protecting group is connected to the eighth amino acid residue. A sulfhydryl protecting group is connected to the N-terminal amino acid residue. The N-terminal amino acid residue is protected by benzyl formyl group. Further, the amino protecting group is a 9-fluorene methoxycarbonyl, the guanidine protecting group is an amantadyl-oxygen carbonyl (Adoc), the carboxyl protecting group is a methyl ester, and the sulfhydryl protecting group is a triphenylmethyl.

In a further embodiment, the step (1) further includes the following sub-steps: dissolving the polypeptide CKGGRAKDC in DMSO (dimethyl sulfoxide), and then adding the polypeptide solution into the triple-necked bottle, dripping N, N-dimethylformamide (DMF) and thionyl chloride into the bottle, stirring evenly, and reacting at 70-75° C. for 1-2 hours to obtain the acyl chloride.

In a further embodiment, dissolving 10 mL of polypeptide CKGGRAKDC (with the amino group, side chain carboxyl group and sulfhydryl group at the N terminus protected) in 1 mL of DMSO to form a polypeptide solution, adding the polypeptide solution into the triple-necked bottle, dripping 2-5 drops of DMF into the bottle, observing a thermometer to control the temperature of the bottle below 25° C.; slowly dripping 3-5 mL of thionyl chloride into the bottle, stirring evenly; then heating up slowly, and reacting at 70-75° C. for 1-2 hours to obtain the acyl chloride, sealing the acyl chloride for later use.

In a further embodiment, the step (2) further includes the following sub-steps: dissolving the verbascoside and the sodium hydroxide in methanol respectively to form two solutions, mixing the obtained completely dissolved solutions, reacting at room temperature to generate sodium phenolate. The chemical structure formula of the verbascoside is shown in formula I. The molar ratio of the verbascoside to the sodium hydroxide is 1:4, so that adequate sodium hydroxide is provided to react with the 4 phenolic hydroxyl groups of the verbascoside.

Formula I

In a further embodiment, introducing 0.1 mol of verbascoside and 0.4 mol of sodium hydroxide into 20 mL of methanol respectively to form two solutions; stirring well until verbascoside and sodium hydroxide are completely dissolved respectively in the methanol, mixing and reacting the obtained solutions of an equal volume at room temperature.

In a further embodiment, the step (3) further includes the following sub-steps: dissolving the sodium phenolate obtained in the step (2) in deionized water to form a solution, stirring well, and then slowly and evenly dripping the acyl chloride obtained in the step (1) into the formed solution at a low temperature, stirring and reacting at 10-15° C. for 1.5-2 hours; after a complete reaction, the adipose tissue-targeting polypeptide is obtained by washing, suction filtering and drying. In a further embodiment, a molar ratio of the adipose tissue-targeting polypeptide obtained in the step (1) to the verbascoside obtained in the step (2) is 1-5:1.

In a further embodiment, at the step (4), the step of modifying the nanogold particle with PEG includes the following sub-steps: mixing the nanogold particle with 2 mL of SH-mPEG-COOH (having a molecular weight of 5000) solution at 20-25° C., stirring and incubating for 12-24 hours; and then removing the unreacted SH-mPEG-COOH by centrifugation and washing for 3 times to obtain a precipitate; dissolving the obtained precipitate in deionized water for later use. A molar ratio of the adipose tissue-targeting polypeptide-verbascoside derivative to the PEG modified nanogold particle is $10^6:9–5$ (the molar ratio is defined by molar weights of the verbascoside and the nanogold). The reaction is carried out under the conditions of shaking overnight away from light with a shaking speed of 200-250 rpm at 20-25° C. The nanogold can inhibit obesity and improve the biocompatibility of the derivative.

Embodiments of the present disclosure further provide an adipose tissue-targeting polypeptide-verbascoside-nanogold particle derivative prepared by the preparation method described above.

Embodiments of the present disclosure further provide an application of the adipose tissue-targeting polypeptide-verbascoside-nanogold particle derivative described above in a preparation of a drug for obesity. In an embodiment, the drug is administered through injection.

Embodiments of the present disclosure have the following advantages: (1) The adipose tissue-targeting polypeptide-verbascoside-nanogold particle derivative has high drug loading and good biocompatibility and is capable of carrying glycoside drugs targetedly into adipocytes, thereby greatly enhancing availability of the drug and significantly improving the targeted anti-obesity activity of the drug. The derivative is suitable for different drug delivery methods. For example, the derivative may function as help targeting in intravenous injection and sustained releasing in intraperitoneal, intramuscular and subcutaneous injections. (2) The materials used in the present disclosure are affordable, and easily available. The preparation process is simple and convenient, which is a routine reaction without destroying properties of drugs themselves. Moreover, the biological properties of the adipose tissue-targeting polypeptide-verbascoside-nanogold particle derivative prepared by the present disclosure is stable and easy to preserve.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE DISCLOSURE

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

Embodiments of the invention are illustrated in detail hereinafter with reference to accompanying drawings. It should be understood that specific embodiments described herein are merely intended to explain the invention, but not intended to limit the invention.

Embodiment 1, the Preparation of the Adipose Tissue-Targeting Polypeptide-Verbascoside-Nanogold Particle Derivative Drugs used: Polypeptides protected by side chains and synthesized by Nanjing Kingsley Biotechnology Co., Ltd.; Nanogold particles purchased from Sigma Co., Ltd.; and Verbascoside purchased from Northwest Plateau Institute of Biology, Chinese Academy of Sciences.

Experimental Procedures:

1) Weighing and dissolving 10 mL of chemosynthetic polypeptide CKGGRAKDC (with the amino group, side chain carboxyl group and sulfhydryl group at the N terminus protected) in 1 mL of DMSO (dimethyl sulfoxide) to form a polypeptide solution, adding the polypeptide solution into the triple-necked bottle provided with a thermometer and a condensation tube, dripping 2-5 drops of DMF into the bottle, observing the thermometer to control the temperature of the bottle below 25° C., and slowly dripping 3-5 mL of thionyl chloride into the bottle, stirring evenly; heating up slowly, reacting at 70-75° C. for 1-2 hours, and cooling to obtain acyl chloride, sealing the acyl chloride for later use;

2) Placing 0.1 mL of verbascoside and 0.4 mL of sodium hydroxide into two 100 mL flasks having 20 mL of methanol respectively, stirring well and evenly until the verbascoside and the sodium hydroxide are respectively completely dissolved in the methanol to form two solutions; mixing and reacting the two solutions with an equal volume at room temperature; bubbling with argon gas while electromagnetic stirring (200 rpm), reducing the pressure using a water pump to dissipate the methanol, cooling and precipitating to room temperature, grinding, and vacuum drying overnight to obtain sodium phenolate, preserving the obtained sodium phenolate in a dryer for later use;

3) Weighing 10 mg of the sodium phenolate and placing the sodium phenolate into a 300 mL triple-necked bottle provided with a thermometer and a condensation tube, adding 30 mL of water, cooling to 0-5° C. after stirring well, slowly and evenly dripping the acyl chloride (a molar ratio of sodium phenolate to acyl chloride is 1:1.5, wherein the sodium phenolate has a molecular weight of 712.59); after half an hour of dripping, sealing and standing the bottle, stirring and reacting at 10-15° C. for 1.5-2 hours. After a complete reaction, filtering the solution, suction filtrating to obtain a filter cake; washing the filter cake with 10-15 mL of deionized water for 3 times; pressing the filter cake to dry to obtain a crude product of adipose tissue-targeting polypeptide-verbascoside derivative; subsequently, placing the obtained crude product and 10 times anhydrous ethanol in volume into a 300 mL round-bottom flask, heating and refluxing to dissolve the crude product thoroughly; adding an appropriate amount of activated carbon in the 300 mL round-bottom flask after cooling; continue heating and refluxing for another 20 minutes; thermal filtering and standing the filtrate to precipitate crystals of the purified adipose tissue-targeting polypeptide-verbascoside derivative, and preserving for later use.

4) Mixing $2 \times 10^{10}$ nanogold particles having a diameter of 20 nm with 5 mL of SH-mPEG-COOH solution (having a concentration of 2 mM) at 25° C.; stirring and incubating for 12 hours; removing the unreacted SH-mPEG-COOH after centrifugation and washing for 3 times to obtain a precipitate, wherein the precipitate is the PEG-modified nanogold particles, dissolving the PEG-modified nanogold particles in deionized water for later use;

5) Dripping potassium carbonate solution having a concentration of 10 wt. % into 10 mL of PEG-modified nanogold particle solution, wherein each nanogold particle has a diameter of 20 nm, adjusting the pH value to 7; then mixing the solution of the adipose tissue-targeting polypeptide-verbascoside derivative dissolved in DMSO (wherein the solution has a concentration of 1 mM; a molar weight of verbascoside is 10 μL) and 1 nM nanogold solution (90 μL), with a volume ratio of 1:9 (after adding potassium carbonate to the PEG-modified nanogold particle solution, the adipose tissue target polypeptide-verbascoside derivative should be added immediately therein to avoid agglomeration of the nanogold), packing with tinfoil away from lights, and shaking evenly overnight with a shaking speed of 200 rpm at 25° C.;

6) Next day, adding PBS (phosphate buffer saline) to each tube to an isochoric volume of 1 mL, transferring the solution to 1.5 mL centrifugal tubes, centrifuging at 4° C. with a speed of 14,000 rpm for 30 minutes, then washing with sterile PBS for 3 times (4° C., 14,000 rpm, 5 minutes), resuspending the derivative by adding 100 μL of PBS therein;

7) TEM detection: preparation of 2% phosphovaleric acid: weighing 0.02 g of phosphovaleric acid and dissolving in 1 mL of water, adjusting the pH to 6-7 using the sodium hydroxide after ultrasonic oscillation; providing three copper nets, dripping the samples on the three copper nets respectively; 5 minutes later, absorbing the water using a filter paper, and re-dying the samples with the 2% phosphovaleric acid for two minutes; draining the water and placing the samples on the filter paper for drying; filming with a magnification of 40000-50000, a scale of 100 nm and an exposure time of 2-3 s.

8) Dynamic light scattering (DLS) detection: diluting the samples to 1 mL with ultra-pure water, and detecting the size of the samples after blowing and mixing evenly.

Figure 1:
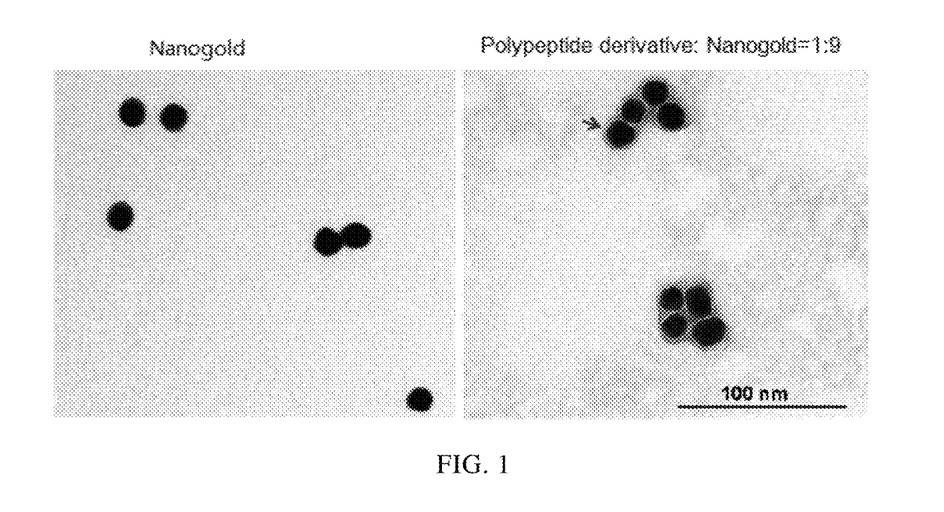
FIG. 1 shows a TEM test of a size of the adipose tissue-targeting polypeptide-verbascoside-nanogold particle derivative. From left to right, the figures show a size of a nanogold particle; a size of the adipose tissue-targeting polypeptide-verbascoside-nanogold particle derivative which is obtained when a volume ratio of the adipose tissue-targeting polypeptide-verbascoside derivative to the nanogold particles is 1:9.
Figure 2:
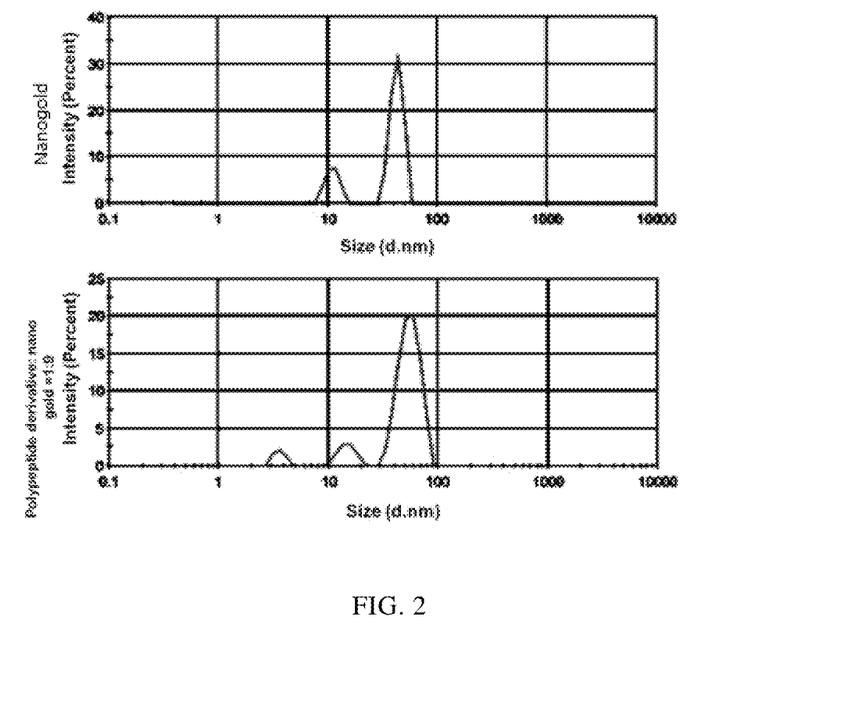
FIG. 2 shows a 1DLS test to determine a size of the adipose tissue-targeting polypeptide-verbascoside-nanogold particle derivative. From up to down, the figures show a size of a nanogold particle; a size of the adipose tissue-targeting polypeptide-verbascoside-nanogold particle derivative which is obtained when a volume ratio of the adipose tissue-targeting polypeptide-verbascoside derivative to the nanogold particles is 1:9.

TEM results are shown in FIG. 1. Compared with pure nanogold particles, there is a layer of adipose tissue-targeting polypeptide-verbascoside derivative enriched on the surface of the nanogold particles of the adipose tissue-targeting polypeptide-verbascoside-nanogold particle derivative (a translucent ring, as indicated by a black arrow). A further analysis of the DLS detection (shown in FIG. 2) illustrates that the particle size peak of the adipose tissue-targeting polypeptide-verbascoside-nanogold particle derivative significantly shifts compared with that of pure nanogold particles, indicating that the adipose tissue-targeting polypeptide-verbascoside derivatives effectively bind with the surface of nanogold particles, which significantly increases the size of the nanogold particles. The TEM results indicate that the adipose tissue-targeting polypeptide-verbascoside-nanogold particle derivative has been successfully constructed.

Embodiment 2, Preparation of the Adipose Tissue-Targeting Polypeptide-Verbascoside-Nanogold Particle Derivative The preparation method is the same as that of Embodiment 1. The differences are that a molar ratio of the sodium phenolate to the acyl chloride in the step (3) is 1:5; and a volume ratio of adipose tissue-targeting polypeptide-verbascoside derivative (calculated by a molar weight of verbascoside) to nanogold particle is 1:5 (10 μL:50 μL).

Embodiment 3, Adipose Tissue-Targeting Polypeptide-Verbascoside-Nanogold Particle Derivative can Effectively Inhibit the Weight Gain of Mice Fed with High-Fat Diet Experimental Animals: 3-4 weeks old male mice and feed provided by the Laboratory Animal Center of Nanjing Medical University, license No.: SCXK (Su) 2011-0003. The animals were randomly caged, with unlimited drink and feed.

Experimental drugs: polypeptide-verbascoside-nanogold particle derivative (adipose tissue-targeting), polypeptide-verbascoside derivative, polypeptide-nanogold derivative, and verbascoside-nanogold derivative as experimental groups, and physiological saline for negative control.

Experimental procedure is provided below:

1) Preparation of polypeptide-verbascoside derivatives, polypeptide-nanogold derivatives, and verbascoside-nanogold derivatives.

a: preparation of polypeptide-verbascoside derivatives: preparing the polypeptide-verbascoside derivatives according to the steps of Embodiment 1;

b: preparation of polypeptide-nanogold derivatives: modifying the nanoparticles with PEG according to step (4) in Embodiment 1 to obtain a precipitate on the bottom, diluting the isopycnic precipitate using 5 mL of deionized water; adjusting the pH value of the 5 mL of 1 nM PEG-modified nanogold solution to 7, using 10 wt. % potassium carbonate solution; subsequently, mixing 10 μL of 1 mM polypeptide solution and 90 μL of 1 nM nanogold solution at a volume ratio of 1:9 at room temperature; shaking overnight away from lights with a shaking speed of 200 rpm at 25° C.; next day, adding PBS to an isochoric volume of 1 mL, centrifuging with a speed of 14000 rpm for 30 minutes at 4° C., then washing with sterile PBS for 3 times (4° C., 14000 rpm, 5 minutes) to obtain a precipitate, which is the polypeptide-nanogold derivative;

c: preparation of verbascoside-nanogold derivatives: modifying the nanoparticles with PEG according to step (4) in Embodiment 1 to obtain a precipitate on the bottom, diluting the isopycnic precipitate using 5 mL of deionized water; adjusting the pH value thereof to 8, using 10 wt. % potassium carbonate solution; heating up to 60° C., and then adding 2 mL of 1 M verbascoside (VB) solution therein for esterification. After esterification for 2 hours, centrifuging to obtain a precipitate on the bottom, wherein the precipitate is a nanogold particle-covalent bond-modified derivative, i.e., the verbascoside-nanogold derivative.

Figure 3:
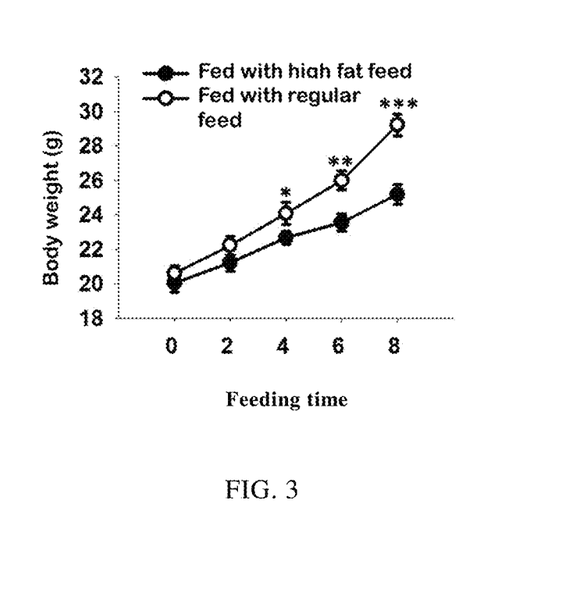
FIG. 3 shows a comparison of weight changes of a group of obese mice fed with high-fat feed and a group of mice fed with regular feed.

2) Raising 60 male mice of 6 weeks old in the clean environment of Experimental Animal Center of Nanjing Medical University, at a temperature of (21±2) ° C., a humidity of (35±2) %, an intermittent illumination for 12 hours, with unlimited drink and feed; wherein the drinking water is distilled water prepared by the experimental animal center;

3) After 2-3 days of adaptive feeding, randomly selecting 10 mice as a blank control group provided with regular feed, while providing the remaining 50 rice with high fat feed (cholesterol 1 wt. %, lard 20 wt. %, bile salt 0.2 wt. %, and regular feed 78.8 wt. %); measuring the body weight of the mice in the two groups every 2 weeks; analyzing the obtained body weight data with statistical methods, and the results are shown in FIG. 3, wherein *P<0.05, P<0.01, and *P<0.001 indicate body weight data of the experimental group compared with those of the blank control group fed with regular feed;

4) Randomly dividing the obese mice fed with high-fat feed into several groups, with each group of 10 mice; injecting (exemplified by intraperitoneal injection) physiological saline (0.03 mL of physiological saline per 30 g body weight), polypeptide-verbascoside derivative (15 mg of derivative per kg body weight, dissolved in DMSO), polypeptide-nanogold derivative (15 mg of derivative per kg body weight, dissolved in DMSO), verbascoside-nanogold derivative (15 mg of derivative per kg body weight, dissolved in DMSO), and polypeptide-verbascoside-nanogold particle derivative (15 mg of derivative per kg body weight, dissolved in DMSO) at 9:30 am every day, respectively. (Note: the doses of the four injected derivatives are the same, so as to exclude differences of toxicity against animals caused by different doses, and thus comparison can be made to figure out which derivative is more effective); except for the blank control group, continue providing the remaining 5 groups with high-fat feed; measuring the body weight of the mice in 6 weeks and 12 weeks after injections respectively; and analyzing the obtained body weight data with statistical methods. The results are shown in Table 1.

TABLE 1

Inhibitory effect of adipose tissue-targeting polypeptide-verbascoside-nanogold particle
derivative on weight gain of mice (the number of mice in each group is 10)

| Groups | Initial Weight (g) | Weight 6 weeks after administration (g) | Weight 12 weeks after administration (g) |
|---|---|---|---|
| Regular feed/blank control group | 25.2 ± 0.5 | 27.3 ± 0.3 | 29.2 ± 1.5 |
| High fat feed + physiological saline group/model control group | 29.1 ± 0.3** | 34.2 ± 0.4** | 40.7 ± 2.1** |
| High fat feed + polypeptide-verbascoside | 29.3 ± 0.5** | 30.6 ± 0.3# | 35.5 ± 1.6# |
| High fat feed + polypeptide-nanogold | 28.8 ± 0.2** | 31.3 ± 0.4# | 36.3 ± 1.2# |
| High fat feed + verbascoside-nanogold | 29.8 ± 0.3** | 30.8 ± 0.2# | 35.1 ± 1.1# |
| High fat feed + polypeptide-verbascoside-nanogold | 29.4 ± 0.4** | 28.1 ± 0.1#$$ | 31.2 ± 0.3#$$ |

Note:
**P < 0.01, indicating a comparison with the blank control group;
P < 0.05, indicating a comparison with the model control group;
$$P < 0.01, indicating a comparison with the other three groups (polypeptide-verbascoside group, polypeptide-nanogold group, verbascoside-nanogold group).

It can be noted from FIG. 3 that after feeding with high-fat feed for 8 weeks, weight gains of the mice were faster than that of the blank control group, and the differences were statistically significant (**p<0.01), indicating that the obesity model was successful. With subsequent treatments using polypeptide-verbascoside derivatives, polypeptide-nanogold derivatives, verbascoside-nanogold derivatives and polypeptide-verbascoside-nanogold particle derivatives for 6 weeks, the weight gains of mice were significantly inhibited. The differences were significant compared with the model control group (#p<0.05). Additionally, compared to the other experimental groups, i.e., the polypeptide-verbascoside derivative group, the polypeptide-nanogold derivative group, and the verbascoside-nanogold derivative group, the polypeptide-verbascoside-nanogold particle derivative can deliver the verbascoside and nanogold particles to the targeted adipose tissues more efficiently (dual drug-loading), which produces a more significant weight-loss effect ($$p<0.01). After administration for 12 weeks, an average body weight of the mice in the group of adipose tissue-targeting polypeptide-verbascoside-nanogold particle derivative was 30.2 g, while an average body weight of the mice in the model control group was 40.7 g. Compared with the blank control group, the body weight differences were 2 g and 11.5 g, respectively, and the body weight inhibition reached (11.5−2)÷11.5×100%=82.6%, indicating that the adipose tissue-targeting polypeptide-verbascoside-nanogold particle derivative inhibited weight gain significantly (see Table 1).

Embodiment 4, Adipose Tissue-Targeting
Polypeptide-Verbascoside-Nanogold Particle
Derivative can Significantly Inhibit the Storage of
Visceral Fat and Subcutaneous Fat of Mice
Provided with High Fat Feed 1) Providing an intraperitoneal administration to the high-fat-fed obese mice for 12 weeks according to the experimental procedure of Embodiment 3;
2) Fasting the mice of each group for 12 hours, and then anesthetizing with 3% pentobarbital sodium having a concentration of 45 mg/kg via intraperitoneal injection, and accurately weighing the mice;
3) Disinfecting routinely and performing laparotomy, rapidly extracting and weighing the adipose tissue around the kidney, adipose tissue around the mesentery, adipose tissue around the epididymis, and abdominal subcutaneous adipose tissue to obtain wet weights thereof (the abdominal subcutaneous adipose tissue range: abdomen below the rib arch and above the groin, both sides are bounded by the midaxillary line);
4) Calculating according to the following formula: wet weight of the abdominal adipose; total weight of the fat pad (g)=adipose tissue around the kidney+adipose tissue around the epididymis; body fat content=the total weight of the fat pad (g)/the total body weight of mice (g);
5) Analyzing the obtained weight data with statistical methods, and the results are shown in Table 2, Table 3 and Table 4.

TABLE 2

Inhibitory effect of adipose tissue-targeting polypeptide-verbascoside-nanoparticle derivative on
the storage of visceral fat and subcutaneous fat of mice (the number of mice in each group is 10)

| Groups | Weight of visceral adipose tissues (g) | | | |
|---|---|---|---|---|
| | Around epididymis | Around kidney | Around omentum and mesentery | Total weight of visceral adipose tissues |
| Regular feed group/blank control group | 0.30 ± 0.11 | 0.07 ± 0.04 | 0.12 ± 0.03 | 0.52 ± 0.16 |
| High fat feed + physiological saline group/model control group | 1.87 ± 0.13** | 0.91 ± 0.14** | 0.58 ± 0.04** | 9.71 ± 0.32** |

TABLE 2-continued

Inhibitory effect of adipose tissue-targeting polypeptide-verbascoside-nanoparticle derivative on
the storage of visceral fat and subcutaneous fat of mice (the number of mice in each group is 10)

| Groups | Weight of visceral adipose tissues (g) | | | |
|---|---|---|---|---|
| | Around epididymis | Around kidney | Around omentum and mesentery | Total weight of visceral adipose tissues |
| High fat feed + polypeptide-verbascoside | 1.21 ± 0.12# | 0.61 ± 0.17# | 0.32 ± 0.05# | 5.72 ± 0.17# |
| High fat feed + polypeptide-nanogold | 1.18 ± 0.15# | 0.68 ± 0.11# | 0.35 ± 0.06# | 5.23 ± 0.11# |
| High fat feed + verbascoside-nanogold | 1.23 ± 0.16# | 0.71 ± 0.10# | 0.38 ± 0.03# | 5.41 ± 0.14# |
| High fat feed + polypeptide-verbascoside-nanogold | 0.61 ± 0.1#$$ | 0.32 ± 0.12#$$ | 0.18 ± 0.02#$$ | 3.13 ± 0.09#$$ |

Note:
**$P < 0.01$, indicating a comparison with the blank control group;
$P < 0.05$, indicating a comparison with the model control group;
$$$P < 0.01$, indicating a comparison with the other three groups (polypeptide-verbascoside group, polypeptide-nanogold group, verbascoside-nanogold group).

TABLE 3

Inhibitory effect of adipose tissue-targeting polypeptide-verbascoside-nanoparticle
derivative on body fat index of mice (the number of mice in each group is 10)

| Groups | Total weight of the fat pad (g) | Body weight (g) | Body fat index (%) |
|---|---|---|---|
| Regular feed group/blank control group | 0.42 ± 0.13 | 29.24 ± 1.48 | 1.32 ± 0.37 |
| High fat feed + physiological saline group/model control group | 3.18 ± 0.20** | 41.91 ± 2.14** | 8.76 ± 0.45** |
| High fat feed + polypeptide-verbascoside | 2.27 ± 0.14# | 35.46 ± 1.57# | 6.13 ± 0.41# |
| High fat feed + polypeptide-nanogold | 2.34 ± 0.11# | 36.26 ± 1.18# | 5.93 ± 0.32# |
| High fat feed + verbascoside-nanogold | 2.21 ± 0.12# | 35.12 ± 1.09# | 6.23 ± 0.13# |
| High fat feed + polypeptide-verbascoside-nanogold | 1.13 ± 0.08#$$ | 30.14 ± 0.54#$$ | 3.12 ± 0.22#$$ |

Note:
**$P < 0.01$, indicating a comparison with the blank control group;
$P < 0.05$, indicating a comparison with the model control group;
$$$P < 0.01$, indicating a comparison with the other three groups (polypeptide-verbascoside group, polypeptide-nanogold group, verbascoside-nanogold group).
Total weight of the fat pad = weight of adipose tissues around kidney + weight of adipose tissues around epididymis; Body fat index = the total weight of the fat pad (g)/the total body weight of mice (g)

TABLE 4

Inhibitory effect of adipose tissue-targeting polypeptide-verbascoside-nanoparticle derivative
on the storage of subcutaneous fat of mice (the number of mice in each group is 10)

| Groups | SF-FAT(g) | VF-FAT(g) | Body weight (g) | SF-FAT/body weight | VF-FAT/SF-FAT |
|---|---|---|---|---|---|
| Regular feed group/blank control group | 0.31 ± 0.11 | 0.52 ± 0.16 | 31.74 ± 1.84 | 0.98 ± 0.26 | 1.75 ± 0.2 |
| High fat feed + physiological saline group/model control group | 1.28 ± 0.26** | 9.71 ± 0.42** | 41.91 ± 2.14** | 3.02 ± 0.35** | 3.36 ± 0.31** |
| High fat feed + polypeptide-verbascoside | 0.79 ± 0.12# | 5.78 ± 0.17# | 35.26 ± 1.77# | 2.27 ± 0.23# | 2.63 ± 0.29# |
| High fat feed + polypeptide-nanogold | 0.71 ± 0.11# | 5.13 ± 0.13# | 36.32 ± 1.78# | 2.31 ± 0.14# | 2.43 ± 0.21# |
| High fat feed + verbascoside-nanogold | 0.74 ± 0.14# | 5.32 ± 0.14# | 37.12 ± 1.79# | 2.19 ± 0.26# | 2.59 ± 0.32# |
| High fat feed + polypeptide-verbascoside-nanogold | 0.41 ± 0.05#$$ | 3.04 ± 0.11#$$ | 32.23 ± 1.12#$$ | 1.06 ± 0.12#$$ | 1.84 ± 0.13#$$ |

Note:
**$P < 0.01$, indicating a comparison with the blank control group;
$P < 0.05$, indicating a comparison with the model control group;
$$$P < 0.01$, indicating a comparison with the other three groups (polypeptide-verbascoside group, polypeptide-nanogold group, verbascoside-nanogold group).

It can be noted from Table 2 that the visceral fat of the model control group fed with high-fat feed, such as fat around the epididymis, fat around the kidney, fat around the omentum and mesentery, increased significantly compared with that of the blank control group, and the difference was statistically significant ($p<0.01$), indicating that obesity causes a large amount of stored visceral fat. After treatments with polypeptide-verbascoside derivatives, polypeptide-nanogold derivatives, verbascoside-nanogold derivatives and polypeptide-verbascoside-nanogold particle derivatives, the wet weight of the visceral adipose tissues of mice was significantly reduced compared with the model control group, and the difference was significant (#p<0.05). Additionally, compared to the other experimental groups, i.e., the polypeptide-verbascoside derivative group, the polypeptide-nanogold derivative group, and the verbascoside-nanogold derivative group, the polypeptide-verbascoside-nanogold particle derivative inhibited the storage of visceral fat of the high-fat fed mice more significantly ($$p<0.01). The body fat indices (F-IDX) of the high-fat fed mice before and after administration of adipose tissue-targeting polypeptide-verbascoside-nanogold particle derivative are shown in Table 3. The body fat content of the model control group was significantly increased (p<0.01) compared to that of the blank control group. After intraperitoneal injection of adipose tissue-targeting polypeptide-verbascoside-nanogold particle derivative, the body fat index of mice was significantly reduced compared with those of the polypeptide-verbascoside derivative group, the polypeptide-nanogold derivative group and the verbascoside-nanogold derivative group, and the difference was significant ($$p<0.01), further indicating that the polypeptide-verbascoside-nanogold particle derivative significantly inhibited the increase in visceral fat of high-fat fed mice. As shown in Table 4, compared with the polypeptide-verbascoside derivative group, polypeptide-nanogold derivative group, and verbascoside-nanogold derivative group, the treatment with adipose tissue-targeting polypeptide-verbascoside-nanogold particle derivative not only reduced the storage of visceral fat of high-fat fed mice, but also reduced the weight of subcutaneous fat of the high-fat fed mice, and decreased the proportion of subcutaneous fat to body weight, and the difference was significant ($$p<0.01). In conclusion, all of the above results indicate that compared with the blank control group, the intra-abdominal visceral fat and abdominal subcutaneous fat of the high-fat fed mice were significantly increased. After treatment with the adipose tissue-targeting polypeptide-verbascoside-nanogold particle derivative, the wet weight of the intra-abdominal visceral fat and abdominal subcutaneous fat of the high-fat fed mice were significantly decreased, whether compared with the model group, or any of the polypeptide-verbascoside derivative group, the polypeptide-nanogold derivative group and the verbascoside-nanogold derivative group. Combined with the results of Embodiment 3, it is further illustrated that the adipose tissue-targeting polypeptide-verbascoside-nanogold particle derivative has a more significant effect on obesity inhibition, that is, it carries drug (verbascoside, nanogold) and targetedly enters the fat cells, and thus greatly enhances the availability of the drugs, thereby significantly increasing the targeted anti-obesity activity of the verbascoside and the nanogold.

Figure 4:
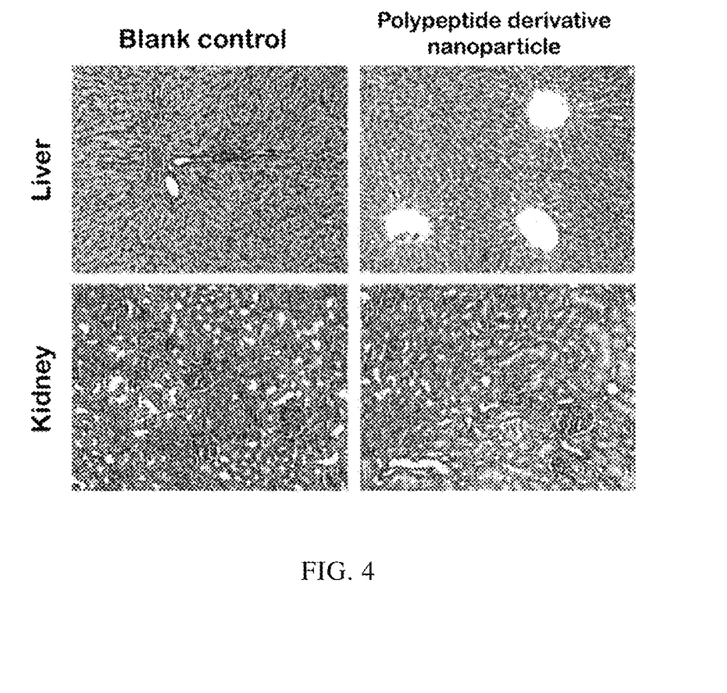
FIG. 4 shows pathological changes in livers and kidneys of the mice in each group examined using H-E staining.

Embodiment 5, Adipose Tissue-Targeting Polypeptide-Verbascoside-Nanogold Particle Derivative has No Obvious Biological Toxicity 1) Providing an intraperitoneal injection to the regularly-fed mice for 12 weeks according to the experimental procedure of Embodiment 3, including injecting the blank control group with physiological saline (0.03 ml of physiological saline per 30 g body weight), and injecting the experimental group with the adipose tissue-targeting polypeptide-verbascoside-nanogold particle derivative (30 mg of the derivative per kg body weight; dissolved in DMSO);

2) Fasting the mice of each group for 12 hours, and then anesthetizing with 3% pentobarbital sodium having a concentration of 45 mg/kg via intraperitoneal injection, disinfecting routinely and performing laparotomy, rapidly extracting liver tissue and the kidney tissue, and observing them after H-E staining; wherein the result is shown in FIG. 4. It can be noted from FIG. 4 (200×) that compared with the blank control group, there were no significant pathological changes in the liver tissue and kidney tissue of the mice injected with the adipose tissue-targeting polypeptide-verbascoside-nanogold particle derivative, indicating that the adipose tissue-targeting polypeptide-verbascoside-nanogold particle derivative has no significant toxic side effects on mice, i.e., it has a good biocompatibility. The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A preparation method of an adipose tissue-targeting polypeptide-verbascoside-nanogold particle derivative, comprising:

activating a carboxyl group of a cysteine residue at a C-terminus of an adipose tissue-targeting polypeptide to form an acyl chloride, wherein the adipose tissue-targeting polypeptide comprises an amino acid sequence of CKGGRAKDC;

reacting a verbascoside with a sodium hydroxide to obtain a sodium phenolate;

esterifying the acyl chloride with the sodium phenolate to form an adipose tissue-targeting polypeptide-verbascoside derivative; and modifying a nanogold particle with polyethylene glycol (PEG), mixing and reacting the adipose tissue-targeting polypeptide-verbascoside derivative with a PEG-modified nanogold particle, wherein the sulfydryl of the cysteine residue at the C-terminus of the adipose tissue-targeting polypeptide is connected to the nanogold particle with an Au—S bond.

2. The preparation method of claim 1, wherein a first amino protecting group is connected to a side chain of a second amino acid residue of the adipose tissue-targeting polypeptide, and a second amino protecting group is connected to a seventh amino acid residue of the adipose tissue-targeting polypeptide;

a guanidine protecting group is connected to the fifth arginine residue;

a carboxyl protecting group is connected to the eighth amino acid residue; and a sulfhydryl protecting group is connected to the N-terminal amino acid residue.

3. The preparation method of claim 2, wherein the amino protecting group is a 9-fluorenylmethoxycarbonyl; the guanidine protecting group is an amantadyl-oxygen carbonyl; the carboxyl protecting group is a methyl ester; and the sulfhydryl protecting group is a triphenylmethyl.

4. The preparation method of claim 1, wherein a molar ratio of the adipose tissue-targeting polypeptide and the verbascoside is 1-5:1.

5. The preparation method of claim 1, wherein the step of modifying the nanogold particle with PEG further comprising:

mixing the nanogold particle with SH-mPEG-COOH at 20-25° C.;

stirring and incubating for 12-24 hours; and removing unreacted SH-mPEG-COOH after centrifugation and washing to obtain a precipitate, wherein the precipitate is the PEG-modified nanogold particle.

6. The preparation method of claim 1, wherein a molar ratio of the adipose tissue-targeting polypeptide-verbascoside derivative and the PEG modified nanogold particle is $10^6$:9-5.

7. A preparation method of an adipose tissue-targeting polypeptide-verbascoside-nanogold particle derivative, comprising:

step (1), activating a carboxyl group of a cysteine residue at a C-terminus of an adipose tissue-targeting polypeptide to form an acyl chloride; wherein the adipose tissue-targeting polypeptide has an amino acid sequence of CKGGRAKDC;

step (2), reacting a verbascoside with a sodium hydroxide to obtain a sodium phenolate;

step (3), esterifying the acyl chloride with the sodium phenolate to form an adipose tissue-targeting polypeptide-verbascoside derivative;

step (4), modifying nanogold particles with polyethylene glycol (PEG), mixing and reacting the adipose tissue-targeting polypeptide-verbascoside derivative with PEG-modified nanogold particles; wherein the sulfydryl of the cysteine residue at the C-terminus of the adipose tissue-targeting polypeptide is connected to the nanogold particles with an Au—S bond;

the step (1) further including: dissolving the polypeptide in Dimethyl Sulfoxide (DMSO) to form a polypeptide solution; adding the polypeptide solution into a bottle, dripping N, N-dimethylformamide (DMF) and thionyl chloride into the bottle and stirring evenly; and reacting at 70-75° C. for 1-2 hours to obtain the acyl chloride;

the step (2) further including: dissolving the verbascoside and the sodium hydroxide in methanol respectively to form two solutions; mixing the two solutions; reacting at room temperature to generate the sodium phenolate; wherein a chemical structure formula of the verbascoside is wherein a molar ratio of the verbascoside to the sodium hydroxide is 1:4;

the step (3) further including: dissolving the sodium phenolate obtained in the step (2) in first deionized water to form a sodium phenolate solution; dripping the acyl chloride obtained in the step (1) into the sodium phenolate solution; stirring and reacting at 10-15° C. for 1.5-2 hours; washing, suction filtering and drying to obtain adipose tissue-targeting polypeptide; wherein a molar ratio of the adipose tissue-targeting polypeptide obtained in the step (1) to the verbascoside obtained in step (2) is 1-5:1; and the step of modifying the nanogold particles with PEG further including: mixing the nanogold particles with a SH-mPEG-COOH solution at 20-25° C., stirring and incubating for 12-24 hours; removing unreacted SH-mPEG-COOH by centrifugation and washing to obtain a precipitate; dissolving the precipitate in second deionized water; wherein a molar ratio of the adipose tissue-targeting polypeptide-verbascoside derivative to the PEG modified nanogold particles is $10^6$:9-5.

* * * * *